United States Patent
Hsiao (10) Patent No.: US 10,413,629 B1
(45) Date of Patent: Sep. 17, 2019

(54) ELECTRICAL WALL SOCKET MOUNTED AROMATIC GAS EMITTING DEVICE

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Dongguan (CN)

( * ) Notice: Subject to any disclaimer, the term of this patent is extended or adjusted under 35 U.S.C. 154(b) by 0 days.

(21) Appl. No.: 16/177,095

(22) Filed: Oct. 31, 2018

(51) Int. Cl.
*A61L 9/14* (2006.01)
*A61L 9/12* (2006.01)

(52) U.S. Cl.
CPC .............. *A61L 9/122* (2013.01); *A61L 9/14* (2013.01); *A61L 2209/12* (2013.01); *A61L 2209/15* (2013.01)

(58) Field of Classification Search
CPC ........ A61L 9/14; A61L 9/122; A61L 2209/12; A61L 2209/15
See application file for complete search history.

(56) References Cited

U.S. PATENT DOCUMENTS

| | | | |
|---|---|---|---|
| 7,963,460 B2 | 6/2011 | Hsiao | |
| 7,992,801 B2 | 8/2011 | Hsiao | |
| 8,029,153 B2 | 10/2011 | Hsiao | |
| 8,133,440 B2 | 3/2012 | Hsiao | |
| 8,196,903 B2 | 6/2012 | Hsiao | |
| 8,201,957 B2 | 6/2012 | Hsiao | |
| 8,765,073 B1 * | 7/2014 | Hsiao | ........................ A61L 2/00 239/34 |
| 9,539,355 B2 | 1/2017 | Hsiao | |
| 2014/0339337 A1 | 11/2014 | Hsiao | |
| 2017/0119919 A1 | 5/2017 | Hsiao | |

* cited by examiner

*Primary Examiner* — Sean E Conley
(74) *Attorney, Agent, or Firm* — Sinorica, LLC (57) ABSTRACT

An electrical wall socket mounted aromatic gas emitting device includes an air bearing seat, a fragrance bottle mounted in the air bearing seat and having a volatile carrier partially inserted into the bottle mouth thereof to absorb the fluid fragrance for dissipation into outside open space, a gas delivery device for continuously delivering air to the air bearing seat so that the air bearing seat can guide the flow of air to flow along the surface of the volatile carrier for agitate the fluid fragrance to emit fragrance smell.

15 Claims, 5 Drawing Sheets

Fig. 5

ELECTRICAL WALL SOCKET MOUNTED AROMATIC GAS EMITTING DEVICE

BACKGROUND OF THE INVENTION

1. Field of the Invention

The present invention relates to scent releasing devices and more specifically, to an electrical wall socket mounted aromatic gas emitting device that emits aromatic gas when switched on after installed in an electrical wall socket.

2. Description of the Related Art

Aromatic gas emitting devices that have excellent aroma volatilization effect and are safe and convenient to use are the products demanded by the market. Conventional aromatic emitting devices, such as aroma nebulizing diffusers, commonly use an oscillator to oscillate a fluid fragrance or essential oil into a fine mist of fragrance that is then delivered into the outside open space by an electric fan. A similar design is seen in U.S. Pat. No. 7,963,460, entitled "Detachable aromatic nebulizing diffuser". Further, there are aromatic gas emitting devices that use a heating element such as an electric resistance to heat an aromatic substance to release a scent. A similar design is seen in U.S. Pat. No. 8,201,957. However, using an electric resistance to heat an aromatic substance must consider electric heating safety. Further, the use of a lamp-based scent releasing system must overcome the limitation of wall socket mounting angle to prevent the fluid fragrance from being poured out.

SUMMARY OF THE INVENTION

The present invention has been accomplished under the circumstances in view. It is therefore an object of the present invention to provide an electrical wall socket mounted aromatic gas emitting device, which has excellent aroma dissipating effect and is safe and convenient to use.

To achieve this and other objects, an electrical wall socket mounted aromatic gas emitting device comprises a bottom housing, an electrical plug assembly, a gas delivery device, and an air bearing seat. The bottom housing comprises an accommodation chamber, an open port and a mounting hole. The interior space of the bottom housing defines the accommodation chamber. The open port is located on the top side of the bottom housing and disposed in communication with the accommodation chamber. The electrical plug assembly is mounted in the mounting hole in one side of the accommodation chamber of the bottom housing. The gas delivery device is mounted in the accommodation chamber of the bottom housing and electrically coupled to the electrical plug assembly. The air bearing seat is mounted in the open port at the top side of the bottom housing, comprising a seat mouth, a wedge chamber, an inner bottom chamber and an air guiding chamber. The seat mouth is formed in the top side of the air bearing seat. The wedge chamber extends from the seat mouth to the inside of the air bearing seat and then extends downward to form the inner bottom chamber. A first communication hole is formed on an inner wall of the wedge chamber. The air bearing seat includes a hollow two-wall structure. Thee air guiding chamber is formed between the two walls of the hollow two-wall structure of the air bearing seat. The air guiding chamber has one side thereof disposed in communication with the first communication hole, and an opposite side thereof provided with a second communication hole. The second communication hole is disposed in communication with the accommodation chamber of the bottom housing.

Further, the accommodation chamber is not a completely enclosed space, it allows the gas delivery device to draw outside air in. The gas delivery device continuously draws outside air through the second communication hole into the air guiding chamber, enabling the intake flow of air to be guided through the first communication hole and the wedge chamber to the outside of the air bearing seat via the seat mouth. Further, an air inlet is located on one side of the bottom housing. The air inlet further assists the gas delivery device to draw outside air in.

Further, the electrical wall socket mounted aromatic gas emitting device is used with a fragrance bottle. The fragrance bottle contains therein a fluid fragrance, comprising a bottle mouth and a volatile carrier. The volatile carrier has one end thereof inserted through the bottle mouth into the inside of the fragrance bottle to touch the fluid fragrance so that the fluid fragrance can be absorbed by the volatile carrier and delivered to an opposite end of the volatile carrier for enabling the fluid fragrance molecules to be dissipated into the outside open air. The fluid fragrance contains general or volatile aromatic liquids. The fragrance bottle further comprises a tubular adapter fastened to the bottle mouth. The volatile carrier has the bottom end thereof inserted through the tubular adapter into the inside of the fragrance bottle.

The bottom side of the fragrance bottle is placed in the inner bottom chamber and kept away from the wedge chamber and the first communication hole by a distance, letting the gas delivery device have a sufficient passage for the gas to be delivered. Through the structural design of the wedge chamber, the fragrance bottle can be conveniently placed in or taken out of the inner bottom chamber. The electrical plug assembly is connected to a power source to provide the gas delivery device with the necessary working electricity. The gas delivery device continuously draws outside air through the second communication hole into the air guiding chamber, enabling the intake flow of air to be guided through the first communication hole and the wedge chamber to the outside of the air bearing seat via the seat mouth. The flow of air that is guided out of the seat mouth flows along the surface of the volatile carrier. The volatile carrier has at least a part thereof disposed in the air flow path. Through the capillary effect of the volatile carrier to attract fluid fragrance molecules, the flow of air that flows along the surface of the volatile carrier carries the fluid fragrance molecules into the outside open air.

The electrical wall socket mounted aromatic gas emitting device does not need to use an electrical heater to heat the fluid fragrance or an oscillator to oscillate the fluid fragrance into a mist of fluid droplets. It uses the air bearing seat to work with the gas delivery device, enabling the fluid fragrance absorbed by the volatile carrier of the fragrance bottle to be continuously carried into the outside open air. This method of use is safe. When the fragrance bottle is exhausted, it can be conveniently taken out of the inner bottom chamber for replacement, and a new fragrance bottle, or a different smell of fragrance bottle can be plugged into the inner bottom chamber for use. Thus, the user can conveniently and rapidly replace the fragrance bottle to enjoy the atmosphere of aromatic gas or to relax the odor in the space.

DETAILED DESCRIPTION OF THE PREFERRED EMBODIMENT

Referring to FIGS. 1-5, an electrical wall socket mounted aromatic gas emitting device in accordance with the present invention is shown. The electrical wall socket mounted aromatic gas emitting device comprises a bottom housing 1, an electrical plug assembly 3, a gas delivery device 5, and an air bearing seat 7.

The bottom housing 1 comprises an accommodation chamber 11, an open port 13 and a mounting hole 15. The interior space of the bottom housing 1 defines the accommodation chamber 11. The open port 13 is located on the top side of the bottom housing 1 and disposed in communication with the accommodation chamber 11.

The electrical plug assembly 3 is mounted between the mounting hole 15 and accommodation chamber 11 of the bottom housing 1.

The gas delivery device 5 is mounted in the accommodation chamber 11 of the bottom housing 1 and electrically coupled to the electrical plug assembly 3.

The air bearing seat 7 mounted in the open port 13 at the top side of the bottom housing 1, comprising a seat mouth 70, a wedge chamber 72, an inner bottom chamber 74 and an air guiding chamber 76. The seat mouth 70 is formed in the top side of the air bearing seat 7. The wedge chamber 72 extends from the seat mouth 70 to the inside of the air bearing seat 7 and then extends downward to form the inner bottom chamber 74. A first communication hole 721 is formed on an inner wall of the wedge chamber 72. The air bearing seat 7 includes a hollow two-wall structure. The air guiding chamber 76 is formed between the two walls of the hollow two-wall structure of the air bearing seat 7. The air guiding chamber 76 has one side thereof disposed in communication with the first communication hole 721, and an opposite side thereof provided with a second communication hole 761. The second communication hole 761 is disposed in communication with the accommodation chamber 11 of the bottom housing 1.

The accommodation chamber 11 is not a completely enclosed space, it allows the gas delivery device 5 to draw outside air in. The gas delivery device 5 continuously draws outside air through the second communication hole 761 into the air guiding chamber 76, enabling the intake flow of air to be guided through the first communication hole 721 and the wedge chamber 72 to the outside of the air bearing seat 7 via the seat mouth 70. In some embodiments, an air inlet 17 is located on one side of the bottom housing 1. The air inlet 17 further assists the gas delivery device 5 to draw outside air in. The gas delivery device 5 can be a fan, a pump or a pneumatic bottle. In the present preferred embodiment, a fan is used for the advantage of optimal air output effect and high safety. Those skilled in the art will be able to replace the fan function with other gas delivery devices such as pumps or air pressure bottles.

The electrical wall socket mounted aromatic gas emitting device is used with a fragrance bottle 71. The fragrance bottle 71 contains therein a fluid fragrance 713, comprising a bottle mouth 711 and a volatile carrier 715. The volatile carrier 715 has one end thereof inserted through the bottle mouth 711 into the inside of the fragrance bottle 71 to touch the fluid fragrance 713 so that the fluid fragrance 713 can be absorbed by the volatile carrier 715 and delivered to an opposite end of the volatile carrier 715 for enabling the fluid fragrance molecules to be dissipated into the outside open air. The fluid fragrance 713 contains general or volatile aromatic liquids.

The bottom side of the fragrance bottle 71 is placed in the inner bottom chamber 74 and kept away from the wedge chamber 72 and the first communication hole 721 by a distance, letting the gas delivery device 5 have a sufficient passage for the gas to be delivered. Through the structural design of the wedge chamber 72, the fragrance bottle 71 can be conveniently placed in or taken out of the inner bottom chamber 74. The electrical plug assembly 3 is connected to a power source to provide the gas delivery device 5 with the necessary working electricity. The gas delivery device 5 continuously draws outside air through the second communication hole 761 into the air guiding chamber 76, enabling the intake flow of air to be guided through the first communication hole 721 and the wedge chamber 72 to the outside of the air bearing seat 7 via the seat mouth 70. The flow of air that is guided out of the seat mouth 70 flows along the surface of the volatile carrier 715. The volatile carrier 715 has at least a part thereof disposed in the air flow path. Through the capillary effect of the volatile carrier 715 to attract fluid fragrance molecules, the flow of air that flows along the surface of the volatile carrier 715 carries the fluid fragrance molecules into the outside open air.

The electrical wall socket mounted aromatic gas emitting device does not need to use an electrical heater to heat the fluid fragrance or an oscillator to oscillate the fluid fragrance into a mist of fluid droplets. It uses the air bearing seat 7 to work with the gas delivery device 5, enabling the fluid fragrance absorbed by the volatile carrier 715 of the fragrance bottle 71 to be continuously carried into the outside open air. This method of use is safe. When the fragrance bottle 71 is exhausted, it can be conveniently taken out of the inner bottom chamber 74 for replacement, and a new fragrance bottle 71, or a different smell of fragrance bottle 71 can be plugged into the inner bottom chamber 74 for use. Thus, the user can conveniently and rapidly replace the fragrance bottle 71 to enjoy the atmosphere of aromatic gas or to relax the odor in the space.

Figure 1:
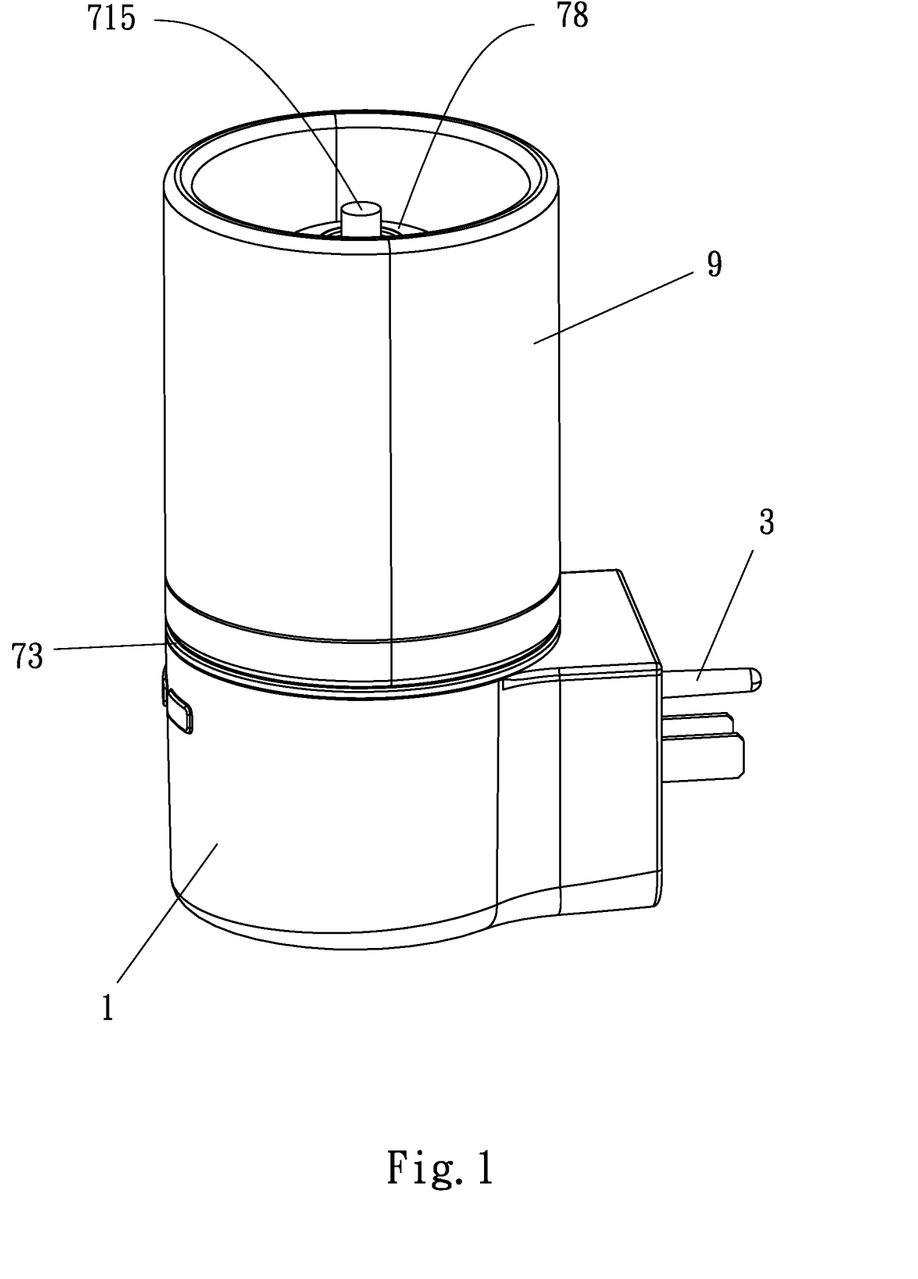
FIG. 1 is an oblique top elevation of exploded view of an electrical wall socket mounted aromatic gas emitting device in accordance with the present invention.
Figure 2:
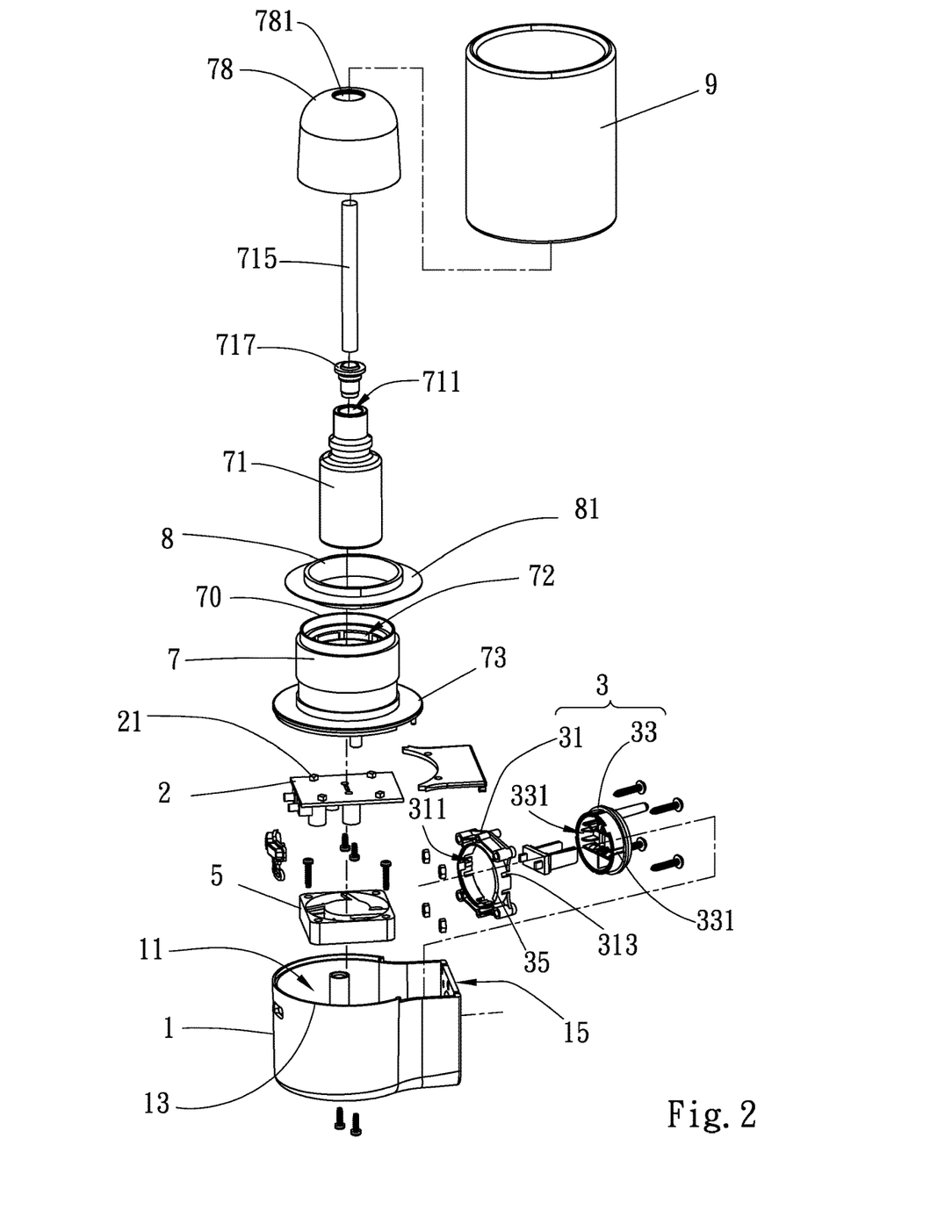
FIG. 2 is an exploded view of the electrical wall socket mounted aromatic gas emitting device in accordance with the present invention.
Figure 3:
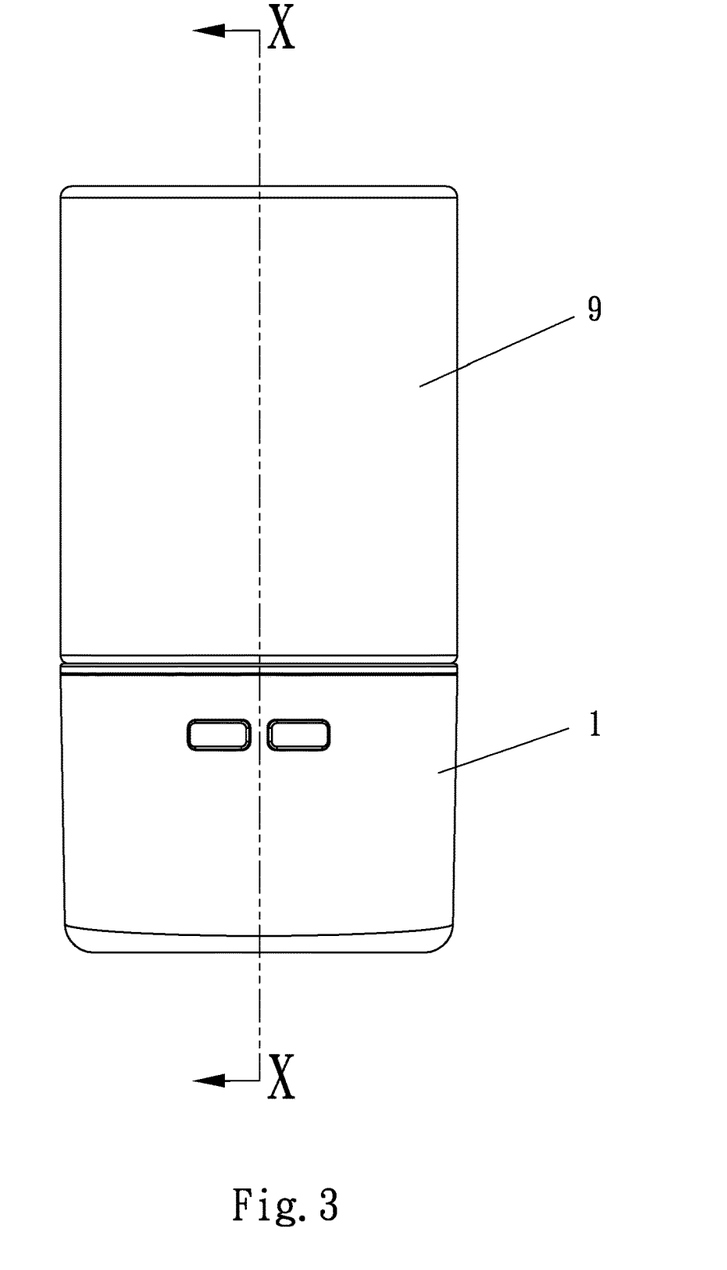
FIG. 3 is a side view illustrating the outer appearance of the electrical wall socket mounted aromatic gas emitting device in accordance with the present invention.
Figure 4:
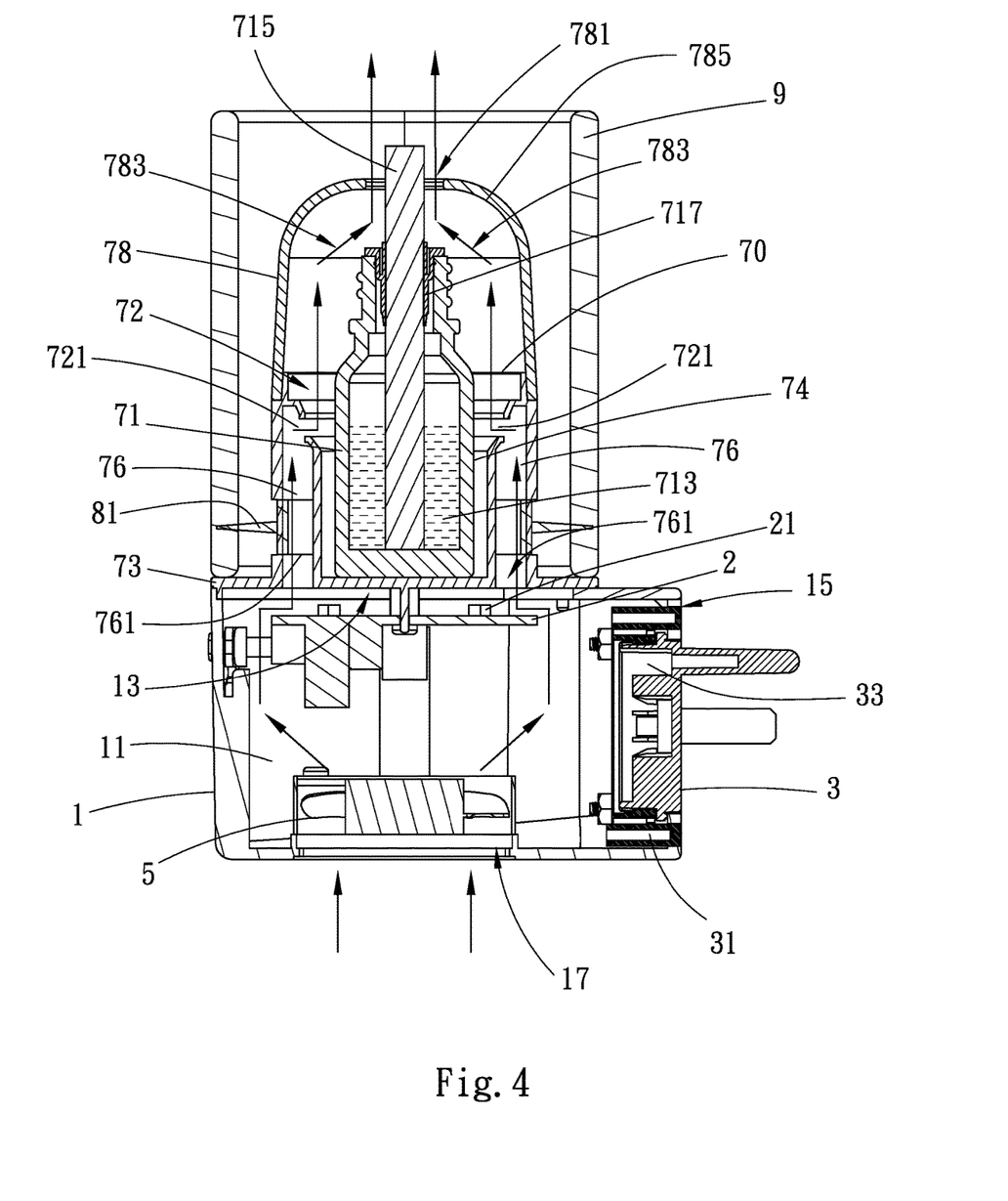
FIG. 4 is a sectional view taken along line X-X of FIG. 3.
Figure 5:
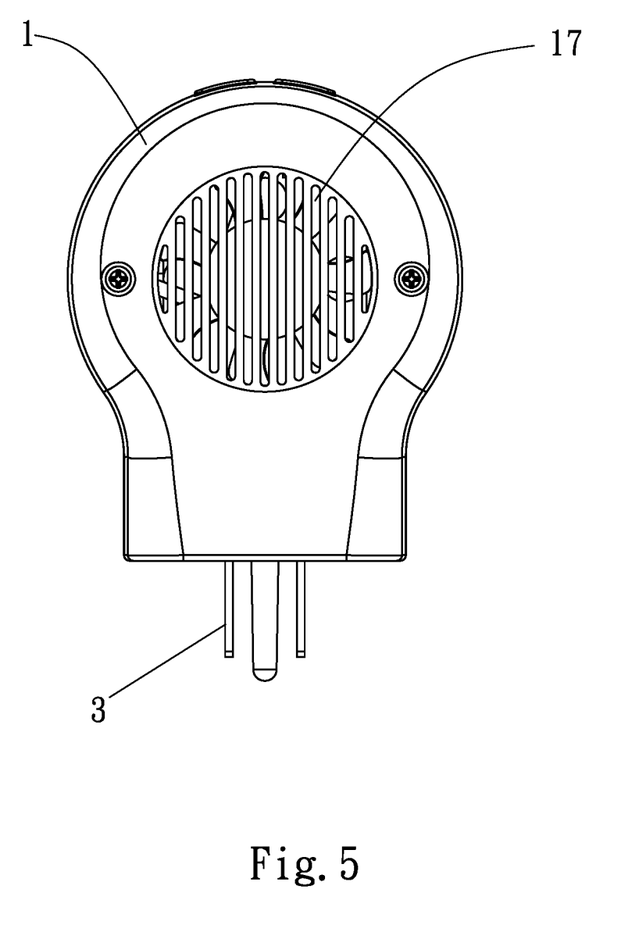
FIG. 5 is a bottom view of the bottom housing of the electrical wall socket mounted aromatic gas emitting device in accordance with the present invention.

Referring to FIG. 2 and FIG. 4, the air bearing seat 7 further comprises a ventilation hood 78. The ventilation hood 78 comprises an air outlet 781, an air dissipation path 783, and a curved lead angle 785. The air outlet 781 is formed on the top side of the ventilation hood 8. The interior space of the ventilation hood 8 defines the air dissipation path 783. The air dissipation path 783 is disposed in communication with the air outlet 781. The curved lead angle 785 is formed on the inner top side of the ventilation hood 78 and extended to the air outlet 781. The ventilation hood 78 has the bottom open side thereof detachably connected to the seat mouth 70 of the air bearing seat 7. When the user places a fragrance bottle 71 in the inner bottom chamber 74 of the air bearing seat 7, the volatile carrier 715 has at least one part thereof extended out of the air outlet 781. An air gap is left between the air outlet 781 and the part of the volatile carrier 715 that extends out of the air outlet 781. Through this air gap, fragrant air can flow out of the electrical wall socket mounted aromatic gas emitting device into the outside open space. Thus, the gas delivery device 5 continuously deliver air through the wedge chamber 72, the seat mouth 70 to the air dissipation path 783 where the curved lead angle 785 concentrates the fragrant airflow, enabling the fragrant airflow to flow through the gap between the air outlet 781 and the volatile carrier 715 to the outside open space. Subject to the effect of the ventilation hood 78, the continuously delivered flow of air flows closely along the surface of the volatile carrier 715 to agitate the fluid fragrance in the volatile carrier 715, thereby effectively emitting fragrant smell. The fluid fragrance can be the type that does not contain volatile agents or has low volatility. Thus, the preferred embodiment of the invention provides excellent fragrance emission.

Referring to FIGS. 2 and 4 again, the electrical plug assembly 3 is a rotary plug structure comprising a pressure ring 31 and a rotary plug 33. The pressure ring 31 comprises a plurality of engaging protrusions 311 spaced around the inner perimeter thereof and respectively located at, for example, 90° angle, 180° angle and 270° angle, and a plurality of buffer notches 313 equiangularly spaced around the periphery. The rotary plug 33 comprises a plurality of retaining grooves 331 spaced around the periphery thereof for the engagement of the engaging protrusions 311. The rotary plug 33 is rotatably mounted within the pressure ring 31 such that the retaining grooves 331 can be shifted with the rotary plug 33 relative to the pressure ring 31 and engaged with the engaging protrusions 311 to secure the rotary plug 33 to the pressure ring 31 in one of a series of angular positions. The rotary plug 33 is electrically coupled with the gas delivery device 5 by, for example, an electrical line. In application, the rotary plug 33 can be inserted into an electrical socket on a wall or at any place where electricity is available. At this time, the user can rotate the bottom housing 1 with the pressure ring 31 relative to the rotary plug 33 to the desired angular position, for example, 90°, 180° or 270° angular position. The design of the buffer notches 313 enhances the flexibility of the pressure ring 31, facilitating rotation and positioning of the rotary plug 33 in the pressure ring 31.

Referring to FIGS. 2 and 4 again, a locating block 35 is disposed within the pressure ring 31 at a location between 270° and 360° angle. Subject to the arrangement of the locating block 35, the engaging protrusions 311 can simply be rotated with the pressure ring 31 relative to the rotary plug 33 within a predetermined range of rotation, for example, from 0° angle to 270° angle, preventing the fragrance bottle 71 from being turned upside down where the bottle mouth 711 faces down and the contained fluid fragrance 713 can be poured out of the fragrance bottle 71. The position of the locating block 35 inside the pressure ring 31 can be changed according to the design needs.

The fluid fragrance 713 can be essential oil, essence, flower essence, perfume or fragrance. The fluid fragrance is preferable a volatile liquid, or a fluid fragrance added with a volatile agent.

Referring to FIGS. 2 and 4 again, the first communication hole 721 is opened on the inner side wall of the wedge chamber 72 in a S-axis direction. The flow of air being continuously delivered by the gas delivery device 5 flows through the second communication hole 761 and the air guiding chamber 76 into the first communication hole 721 and is then turned into a horizontal airflow that impacts the fragrance bottle 71 and then flows vertically upward along the surface of the volatile carrier 715 of the fragrance bottle 71 to form an aromatic air dissipation path.

Referring to FIGS. 2 and 4 again, the air bearing seat 7 and the air guiding chamber 76 have a cylindrical structure; the second communication hole 761 is formed into a ring-shaped communication port structure; the first communication hole 721 is a ring-shaped communication port structure inside the wedge chamber 72; the airflow being continuously delivered by the gas delivery device 5 is delivered into the second communication hole 761 to flow through the air guiding chamber 76, the first communication hole 721 into the wedge chamber 72 and then the seat mouth 70 around the surface of the volatile carrier 715. Therefore, the airflow can flow along the surface of the volatile carrier 715 to produce a better fragrant aroma effect.

Referring to FIGS. 2 and 4 again, the first communication hole 721 consists of a plurality of spaced pores. The flow rate of gas continuously delivered through the first communication hole 721 at the same time is less than the flow rate of gas entering the air guiding chamber 76 from the second communication hole 761. Therefore, gas pressure is accumulated in the air guiding chamber 76. The spaced pores of the first communication hole 721 accelerates the jetted output airflow to the surface of the volatile carrier 715 to agitate the fluid fragrance around the surface of the volatile carrier 715. Especially for the less volatile fluid fragrance, the agitation disturbance can produce a better effect to agitate the fluid fragrance into fragrance molecules.

Referring to FIGS. 2 and 4 again, the electrical wall socket mounted aromatic gas emitting device further comprises a circuit board 2 and a light-emitting device 21. The light-emitting device 21 and the circuit board 2 are electrically coupled together. The circuit board 2 is electrically coupled to the electrical plug assembly 3. The circuit board 2 and the light-emitting device 21 are mounted in the accommodation chamber 11 of the bottom housing 1. An air gap is defined between the circuit board 2 and the open port 13 for the passing of air so that the circuit board 2 does not block air from passing through the open port 13. The air bearing seat 7 is selected from a light transmissive or translucent material. Further, a light guide 713 extends around the periphery of the air bearing seat 7.

Referring to FIGS. 2 and 4 again, the electrical wall socket mounted aromatic gas emitting device further comprises a support ring 8 and a cap 9. The cap 9 is a double open-end structure. The support ring 8 has a flange 81 extending around the periphery thereof. The flange 81 is elastic. The support ring 8 is attached onto the outside wall of the air bearing seat 7. The cap 9 is adapted to cover the air bearing seat 7 and the support ring 8. The cap 9 has the inside wall thereof configured to elastically fit the outer perimeter of the support ring 8. It can be detachably fastened to the flange 81 of the support ring 8 by press-fitting. The support ring 8 is used to stabilize the cap 9. The cap 9 is used to close or open the air bearing seat 7. Thus, the cap 9 can protect the internal components of the electrical wall socket mounted aromatic gas emitting device and can also be used as a decorative cover. The support ring 8 can be a silicon rubber ring, rubber ring or plastic ring, or a ring structure made of an elastically deformable or softly deformable material. Thus, the cap 9 can be conveniently closed or opened, facilitating quick displacement of the fragrance bottle 71. As the cap 9 can be conveniently and detachably fastened to the support ring 8 by press-fitting, caps 9 of different colors, different patterns or different materials can be selectively used to create different decorative effects.

When the cap 9 is capped on the outside wall of the air bearing seat 7, the bottom edge of the cap 9 is secured to the top side of the light guide 713. Further, the open port 13 of the bottom housing 1 is secured to the bottom side of the light guide 713. Thus, the electrical plug assembly 3 can be connected to a power source (power socket) to provide electricity to the circuit board 2 for driving the light-emitting device 21 to emit light. The air bearing seat 7 receives the light to produce a vignetting effect. The light guide 713 displays the vignetting on the outside of the electrical wall socket mounted aromatic gas emitting device to form a decorative effect of the light guide 713. The light-emitting device 21 can be a LED, a lamp bulb, or any other means that can be activated to emit light.

Referring to FIGS. 1-4 again, the electrical wall socket mounted aromatic gas emitting device is equipped with a fragrance bottle 71. The fragrance bottle 71 contains therein a fluid fragrance 713, comprising a bottle mouth 711 and a volatile carrier 715. The volatile carrier 715 has one end thereof inserted through the bottle mouth 711 into the inside of the fragrance bottle 71 to contact the fluid fragrance, thereby guiding the fluid fragrance 713 to the other end of the volatile carrier 715.

Referring to FIGS. 1-4 again, the fragrance bottle 71 used in the electrical wall socket mounted aromatic gas emitting device further comprises a tubular adapter 717 fastened to the bottle mouth 711. The volatile carrier 715 has one end thereof inserted through the tubular adapter 717 into the inside of the fragrance bottle 71. Thus, the other end of the volatile carrier 715 is steadily supported by the tubular adapter 717 in a standing position for effectively emitting a fragrant smell. The tubular adapter 717 is selected from an elastic material such as silicone, rubber or elastic cotton.

The volatile carrier 715 is selectively made of one of various materials such as cotton core, cotton swab, absorbent cloth, fiber rod, foam or paper material, which can absorb the fluid fragrance 713 and emit liquid fragrance molecules. In some implementations, the volatile carrier 715 is in the form of a rod or strip to facilitate contact with the fluid fragrance 713 in the bottle mouth 711.

Although a particular embodiment of the present invention has been described in detail for purposes of illustration, various modifications and enhancements may be made without departing from the spirit and scope of the invention. Accordingly, the invention is not to be limited except as by the appended claims.

What the invention claimed is:

1. An electrical wall socket mounted aromatic gas emitting device, comprising:
   a bottom housing, said bottom housing comprising an accommodation chamber defined in an internal space thereof, an open port located on a top side thereof in communication with said accommodation chamber and a mounting hole located on one lateral side thereof;
   an electrical plug assembly mounted between said accommodation chamber and said mounting hole of said housing;
   a gas delivery device mounted in said accommodation chamber of said bottom housing and electrically coupled to said electrical plug assembly; and
   an air bearing seat mounted in said open port at the top side of said bottom housing, said air bearing seat comprising a seat mouth, a wedge chamber, an inner bottom chamber and an air guiding chamber, said seat mouth being formed in a top side of said air bearing seat, said wedge chamber extending from said seat mouth to the inside of said air bearing seat and then extending downward to form said inner bottom chamber, said wedge chamber having a first communication hole formed on an inner wall thereof, said air bearing seat being a hollow two-wall structure, said air guiding chamber being formed between the two walls of said hollow two-wall structure of said air bearing seat, said air guiding chamber having one side thereof disposed in communication with said first communication hole and an opposite side thereof provided with a second communication hole, said second communication hole being disposed in communication with said accommodation chamber of said bottom housing.

2. The electrical wall socket mounted aromatic gas emitting device as claimed in claim 1, wherein said air bearing seat further comprises a ventilation hood, said ventilation hood comprising an air outlet, an air dissipation path and a curved lead angle, said air outlet being formed on a top side of said ventilation hood, said air dissipation path being defined inside said ventilation hood and disposed in communication with said air outlet, said curved lead angle being formed on an inner top side of said ventilation hood and extended to said air outlet, said ventilation hood having a bottom open side thereof detachably connected to said seat mouth of said air bearing seat.

3. The electrical wall socket mounted aromatic gas emitting device as claimed in claim 2, wherein said first communication hole is opened on the said inner side wall of said wedge chamber in a S-axis direction.

4. The electrical wall socket mounted aromatic gas emitting device as claimed in claim 2, wherein said air bearing seat and said air guiding chamber have a cylindrical structure; said second communication hole is ring-shaped; said first communication hole is a ring-shaped communication port structure inside said wedge chamber.

5. The electrical wall socket mounted aromatic gas emitting device as claimed in claim 1, wherein said electrical plug assembly is a rotary plug structure, comprising a pressure ring mounted in said mounting hole of said bottom housing and a rotary plug rotatably mounted within said pressure ring, said pressure ring comprising a plurality of engaging protrusions spaced around an inner perimeter thereof and a plurality of buffer notches located on and spaced around the periphery thereof, said rotary plug comprising a plurality of retaining grooves spaced around the periphery thereof and selectively engaged with said engaging protrusions to secure said rotary plug to said pressure ring in one of a series of angular positions.

6. The electrical wall socket mounted aromatic gas emitting device as claimed in claim 1, wherein said first communication hole is opened on the said inner side wall of said wedge chamber in a S-axis direction.

7. The electrical wall socket mounted aromatic gas emitting device as claimed in claim 1, wherein said air bearing seat and said air guiding chamber have a cylindrical structure; said second communication hole is ring-shaped; said first communication hole is a ring-shaped communication port structure inside said wedge chamber.

8. The electrical wall socket mounted aromatic gas emitting device as claimed in claim 7, wherein said first communication hole consists of a plurality of spaced pores.

9. The electrical wall socket mounted aromatic gas emitting device as claimed in claim 1, further comprising a circuit board and a light-emitting device, said light-emitting device and said circuit board being electrically coupled together, said circuit board being electrically coupled to said electrical plug assembly, said circuit board and said light-emitting device being mounted in said accommodation chamber of said bottom housing, wherein said air bearing seat is selectively made of a light transmissive or translucent material; said air bearing seat comprises a light guide extending around the periphery thereof.

10. The electrical wall socket mounted aromatic gas emitting device as claimed in claim 9, further comprising a support ring and a cap, said cap being a double open-end structure, said support ring comprising a flexible flange around the periphery thereof, said support ring being attached onto an outside wall of said air bearing seat, said cap being adapted to cover said air bearing seat and said support ring and so configured that when said cap is capped on said air bearing seat, a bottom edge of said cap is secured to a top side of said light guide of said air bearing seat and an opposing bottom side of said light guide is secured to said open port of said bottom housing.

11. The electrical wall socket mounted aromatic gas emitting device as claimed in claim 1, further comprising a fragrance bottle, said fragrance bottle holding therein a fluid fragrance, said fragrance bottle comprising a bottle mouth and a volatile carrier, said volatile carrier having a bottom end thereof inserted through said bottle mouth into the inside of said fragrance bottle to touch said fluid fragrance to being said fluid fragrance to be guided to an opposite end of said volatile carrier.

12. The electrical wall socket mounted aromatic gas emitting device as claimed in claim 11, wherein said fragrance bottle further comprises a tubular adapter fastened to said bottle mouth; said volatile carrier has the bottom end thereof inserted through said tubular adapter into the inside of said fragrance bottle.

13. The electrical wall socket mounted aromatic gas emitting device as claimed in claim 12, wherein said fragrance bottle further comprises a tubular adapter fastened to said bottle mouth; said volatile carrier has the bottom end thereof inserted through said tubular adapter into the inside of said fragrance bottle.

14. The electrical wall socket mounted aromatic gas emitting device as claimed in claim 13, wherein said fragrance bottle further comprises a tubular adapter fastened to said bottle mouth; said volatile carrier has the bottom end thereof inserted through said tubular adapter into the inside of said fragrance bottle.

15. The electrical wall socket mounted aromatic gas emitting device as claimed in claim 14, wherein said fragrance bottle further comprises a tubular adapter fastened to said bottle mouth; said volatile carrier has the bottom end thereof inserted through said tubular adapter into the inside of said fragrance bottle.

* * * * *